United States Patent [19]

Leonidov

[11] Patent Number: 5,453,532
[45] Date of Patent: Sep. 26, 1995

[54] CRYSTALLINE MODIFICATION OF 2-DIMETHYLAMINOETHYL-N-BUTYLAMINOBENZOATE HYDROCHLORIDE, METHOD FOR PRODUCTION THEREOF AND PHARMACEUTICAL PREPARATION FOR ANAESTHESIA OF EYES, BASED THEREON

[76] Inventor: Nikolai B. Leonidov, ulitsa Zatonnaya, 12, korpus 1, kv.158, Moscow, Russian Federation

[21] Appl. No.: 281,063

[22] Filed: Jul. 26, 1994

Related U.S. Application Data

[62] Division of Ser. No. 958,106, Dec. 22, 1992.

[30] Foreign Application Priority Data

Apr. 30, 1991 [RU] Russian Federation ............... 4927838
Apr. 30, 1991 [RU] Russian Federation ............... 4927859

[51] Int. Cl.⁶ .................................................. C07C 229/10
[52] U.S. Cl. ................................................................ 560/49
[58] Field of Search ................................................. 560/49

OTHER PUBLICATIONS

Owens, J. Ass. Off. Anal. Chem. 55(6) 1171–4. (1972).
Machkovsky, M.D. "Medications". vol. 1, 1986 Meditsina (Moscow), pp. 325–328.
International Pharmacopoeia, 3rd ed., vol. 3, "Specification for Controlling Quality of Pharmaceutical Preparations".
Rubtsov, M. V. et al. "Synthetic Chemical . . . Substances," Meditsina Publishers Moscow, 1971, pp. 73–77.
Zurini, R. et al. "Thermal Analytical Techniques . . . Analysis", Thermochimica Acta, 153 (1989) pp. 11–26.

*Primary Examiner*—José G. Dees
*Assistant Examiner*—Joseph M. Conrad, III
*Attorney, Agent, or Firm*—Ladas & Parry

[57] ABSTRACT

A novel crystalline modification of 2-dimethylaminoethyl-n-butylaminobenzoate hydrochloride is characterized by a melting point of 148.6°±0.3° C. and has an interplanar spacing d and relative intensities defined herein, and a method for making said crystal. The compound of the invention is has local anaesthetic activity and is an active principle of a pharmaceutical preparations for the eyes.

10 Claims, No Drawings

CRYSTALLINE MODIFICATION OF 2-DIMETHYLAMINOETHYL-N-BUTYLAMINOBENZOATE HYDROCHLORIDE, METHOD FOR PRODUCTION THEREOF AND PHARMACEUTICAL PREPARATION FOR ANAESTHESIA OF EYES, BASED THEREON

This application is a divisional of Ser. No. 07/958,106 filed Feb. 2, 1992, which is a 371 of PCT/US91/00168 filed Aug. 19, 1991.

TECHNICAL FIELD

The present invention relates to organic chemistry, more particularly to a novel crystalline modification of 2-dimethylaminoethyl-n-butylaminobenzoate hydrochloride, a method of production thereof and a pharmaceutical preparation for anaesthesia of eyes, base thereon.

BACKGROUND ART

Known in the art is a crystalline modification of 2-dimethylaminoethyl-n-butylaminobenzoate hydrochloride (tetracaine), polymorphic form (R. C. Sullivan, K. P. O'Brien. X-ray diffraction studies of cocaone and its substitutes.—Bull.Narcotics, 1968, V.20, pp. 31—40), characterized, by the following set of interplanar spacings d and relative intensities of reflections I:

| d, Å | I |
|---|---|
| 12.55 | 100 |
| 8.38 | 42 |
| 6.28 | 12 |
| 5.42 | 8 |
| 5.05 | 67 |
| 4.83 | 12 |
| 4.43 | 8 |
| 4.22 | 20 |
| 3.97 | 11 |
| 3.78 | 10 |
| 3.56 | 8 |
| 3.48 | 17 |
| 3.30 | 10 |
| 3.12 | 10 |
| 2.96 | 6 |
| 2.805 | 7 |
| 2.661 | 5 |
| 2.507 | 5 |
| 2.151 | 4 |
| 1.949 | 4 |

Also known in the art is a crystalline modification of 2-dimethylaminoethyl-n-butylaminobenzoate hydrochloride (amethocaine), polymorphic form (I. T. R. Owen, R. Sithiraks, F. A. Underwood. X-ray powder diffraction data for seventeen local anesthetics—I.Ass.Off Analyt. Chem., 1972, V.55) characterized by the following set of interplanar spacings d and relative intensities of reflections I:

| d, Å | I | d, Å | I |
|---|---|---|---|
| 13.3 | 10 | 3.22 | 7 |
| 8.06 | 10 | 3.17 | 10 |
| 6.55 | 40 | 3.08 | 9 |
| 6.23 | 20 | 3.03 | 7 |
| 6.02 | 40 | 3.00 | 7 |
| 5.73 | 6 | 2.94 | 4 |
| 5.07 | 6 | 2.87 | 6 |
| 4.78 | 15 | 2.82 | 12 |
| 4.50 | 25 | 2.77 | 9 |
| 4.39 | 13 | 2.71 | 6 |
| 4.23 | 20 | 2.66 | 7 |
| 4.05 | 15 | 2.62 | 6 |
| 3.98 | 18 | 2.58 | 6 |
| 3.83 | 25 | 2.54 | 7 |
| 3.73 | 12 | 2.50 | 4 |
| 3.65 | 100 | 2.46 | 6 |
| 3.57 | 10 | 2.42 | 6 |
| 3.45 | 20 | 2.32 | 6 |
| 3.40 | 7 | 2.28 | 6 |
| 3.28 | 6 | 2.24 | 6 |
|  |  | 2.15 | 6 |

Melting point of specified modifications is in the range of from 147° to 15° C. In this case, the process of melting of these modifications is a sequence of two endothermal effects (R. Curini, S. Zamponi, F. D'Ascenzo, S. De Angelis Curtis, A. Marino, A. Dezzi, Thermal analytical techniques applied to the narcotic field: cocaine analysis.—Thermochim. Acta, 1989, V.153, N I, pp. 11–26).

Known in the art is a method for production of said modifications of 2-dimethylaminoethyl-n-butylaminobenzoate hydrochloride, comprising a process of n-butylation of β-dimethylaminoethyl-para-aminobenzoate with subsequent crystallization of the obtained product in the mixture with hydrosulfite and carbon from ethyl alcohol at 2°–3° C. and drying (Synthetic chemico-pharmaceutical preparations, "Meditsina", (Moscow), 1971, pp. 75–77)

The obtained product represents the aforementioned crystalline modifications characterized by the specified set of values d and I. Melting point of the obtained compound is in the range of 147°–15° C. with two subsequent endothermal effects.

The obtained product is a white crystalline powder having a slightly bitter taste, which causes temporary anaesthesia of the tongue, soluble in water and alcohol, moderately soluble in chloroform and practically insoluble in ether.

The known crystalline modifications of said compound, showing an effect of local anaesthesia, are highly toxic.

Besides, the known modifications of said compound have considerable side effects and when pharmaceutical preparations based on these compounds are used in ophthal-mosurgery, they cause eyelid edema, injury to cornea epithelium, erosions, considerable dilation of conjuctiva. Eye drops based on these compounds are unstable in storage (term of validity is 3 months on condition of additional stabilization of the solution).

The crystalline modification of 2-dimethylaminoethyl-n-butylaminobenzoate hydrochloride according to the invention, method of its production and application are novel and haven't been described in the literature.

SUMMARY OF THE INVENTION

The invention is based on the problem to provide a novel crystalline modification of 2-dimethylaminoethyl-n-butylaminobenzoate hydrochloride showing a high local anaesthetic effect, having no side effects, as well as to provide a method for production of this modification and a pharmaceutical preparation based thereon.

The problem is solved by that provided is a novel crystalline modification of 2-dimethylaminoethyl-n-butylaminobenzoate hydrochloride, characterized by a single endothermal effect of melting at 148.6±0.3° C. and the following values of interplanar spacings d and relative intensities of reflections I:

| I | d, Å | I | d, Å |
|---|------|---|------|
| 3 | 26.140 | 4 | 2.824 |
| 100 | 12.755 | 2 | 2.798 |
| 27 | 8.538 | 1 | 2.762 |
| 6 | 6.380 | 2 | 2.744 |
| 2 | 6.117 | 2 | 2.678 |
| 6 | 5.644 | 1 | 2.631 |
| 12 | 5.491 | 1 | 2.570 |
| 56 | 5.096 | 1 | 2.534 |
| 17 | 4.874 | 1 | 2.514 |
| 10 | 4.486 | 1 | 2.454 |
| 15 | 4.244 | 1 | 2.419 |
| 7 | 4.418 | 1 | 2.346 |
| 1 | 4.137 | 1 | 2.308 |
| 5 | 4.001 | 1 | 2.256 |
| 3 | 3.949 | 1 | 2.232 |
| 5 | 3.828 | 1 | 2.166 |
| 3 | 3.585 | 1 | 2.006 |
| 7 | 3.515 | 2 | 1.953 |
| 3 | 3.427 | 1 | 1.691 |
| 3 | 3.341 | 1 | 1.584 |
| 3 | 3.310 | | |
| 3 | 3.170 | | |
| 4 | 3.156 | | |
| 4 | 3.149 | | |
| 1 | 3.064 | | |
| 2 | 2.979 | | |
| 1 | 2.944 | | |
| 1 | 2.903 | | |

The invention is also a method for production of a novel crystalline modification of specified compound, which method, according to the present invention, resides in that a solution of 2-dimethylaminoethyl-n-butylaminobenzoate hydrochloride of polymorphic form in water or an organic solvent, or in their mixture is cooled by a cooling agent at rate of no less than 8° C./ mill till complete crystallization with subsequent isolation of the obtained crystals and their drying. In doing so, it is desirable to use ethanol as an organic solvent and liquid nitrogen, as a cooling agent. Drying is preferably carried out in vacuo at a pressure of no more than $10^{-2}$ mm Hg.

The obtained novel crystalline modification of 2-di-methylaminoethyl-n-butylaminobenzoate hydrochloride shows higher local anaesthetic activity and considerably reduced side effects as compared with the known polymorphic form of the indicated compound.

The novel crystalline modification of said compound according to the present invention finds application in ophthalmology.

A pharmaceutical preparation for anaesthesia of eyes containing an active ingredient and a pharmaceutical solvent, according to the present invention, as an active ingredient comprises the claimed crystalline modification of 2-dimethylaminoethyl-n-butylaminobenzoate hydrochloride in amount of from 0.05 to 0.5% by mass.

With the aim to effectively use the active ingredient and to increase a prolongated effect, the preparation of the invention may additionally contain alkylcellulose in amount of from 0.1 to 0.75% by mass.

As alkylcellulose, the preparation of the invention preferably contains water-soluble methylcellulose.

The preparation of the invention has high local anaesthetic activity, practically doesn't cause side effects.

High local anaesthetic activity of the active ingredient allows to reduce its concentration in the claimed pharmaceutical preparation as compared with the known preparation on the base on other modifications (of polymorphic form) by a factor of three and more, which fact considerably decreases toxicity of the preparation. The preparation of the invention is characterized by stability in storage which makes it possible to prolong its term of validity (more than 1 year).

Best Mode to Carry out the Invention

The novel crystalline modification of 2-dimethylaminoethyl-n-butylaminobenzoate hydrochloride according to the present invention is a finest crystalline powder of white colour, soluble in water and alcohol, practically insoluble in ether. Unlike known crystalline modifications, this modification is soluble in chloroform. 1% aqueous solution of the claimed modification has a pH value in 4.5–6.0 range.

As distinct from the known polymorphic forms, the obtained novel crystalline modification is characterized by a single endothermal effect of melting at a temperature of 148.6±0.3° C.

Process of melting of the known crystalline modifications of the specified compound, said modifications having melting point in the range of 147°–152° C., is a sequence of two endothermal effects.

The obtained thermoanalytical data evidence that the compound of the invention is a novel crystalline modification of 2-dimethylaminoethyl-n-butylaminobenzoate hydrochloride.

To identify the claimed compound, a complex of chemical, physico-chemical and pharmacopoeia methods of analysis was employed.

To confirm the novel crystalline modification of the the compound of the invention, a radiographic phase analysis in Guinier camera with registration of diffraction peaks on a radiographic film was used.

Comparison of the values of interplanar spacings d and relative intensities of reflections I of the compound of the invention and of the known modifications proves that the compound of the invention is a novel crystalline modification of 2-dimethylaminoethyl-n-butylaminobenzoate hydrochloride.

Using the methods of qualitative and quantitative determination, it was found that the compound of the invention is 2-dimethylaminoethyl-n-butylaminobenzoate hydrochloride of 99.8% purity.

These data are confirmed by the high resolution NMR$^{13}$C spectroscopy and gas chromatography methods.

High resolution NMR$^{13}$C spectra were measured on a NMR-spectrometer with a superconducting magnet, observation frequency for carbon nuclei 131.00 MHz. Measurements of chemical shifts NMR$^{13}$C–I$_H$ of the samples of the known modification and of the claimed one of the specified compound was carried out using their saturated solutions in deuterodimethylsulfoxide DMSO-D$_6$ with 0.01 ppm accuracy. Values of NMR$^{13}$C chemical shifts were measured in relation to the solvent signal and calculated according to TMS-scale (TMS-Si(CH$_3$)$_4$)β$_{TMS}$=β$_{DMSO}$–39.56 ppm. The values of the chemical shifts are presented in Table 1. Analysis of NMR$^{13}$C-spectra of the studied samples of the known and claimed modifications of the cited compound has shown that no impurities were observed on the signal/noise= 100 ratio level.

The given data allow to conclude that the novel compound according to the present invention has a chemical formula identical with that of the specified compound.

TABLE 1

Chemical Shifts of Carbon $^{13}$C Nuclei of the Known and Claimed Crystalline Modifications of 2-Dimethylaminoethyl-n-Butylamino-benzoate Hydrochloride

| Nos. | Compound | Position of carbon atom in molecule of specified compound |
|---|---|---|

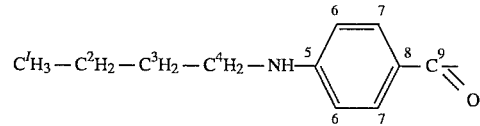

| | | $C^1$ | $C^2$ | $C^3$ | $C^4$ | $C^5$ | $C^{6*}$ |
|---|---|---|---|---|---|---|---|
| 1 | 2 | 3 | 4 | 5 | 6 | 7 | 8 |
| 1 | Known modification | 14.27 | 20.25 | 31.05 | 42.55 | 153.94 | 111.42 |
| 2 | Modification of the present invention | 13.75 | 19.76 | 30.57 | 41.94 | 153.31 | 110.74 |

| | $C^{7*}$ | $-OC^{10}H_2-C^{11}H_2-(C^{12}H_3)_2 \cdot HCl$ | | | | |
|---|---|---|---|---|---|---|
| | | $C^8$ | $C^9$ | $C^{10}$ | $C^{11}$ | $C^{12*}$ |
| 1 | 9 | 10 | 11 | 12 | 13 | 14 |
| 1 | 232.29 | 115.06 | 166.37 | 58.80 | 56.10 | 43.46 |
| 2 | 131.48 | 114.63 | 165.63 | 58.30 | 55.08 | 42.53 |

\* - given values correspond to two equivalent atoms of carbon - 13.

Retention time was measured on highly efficient capillary column with nonpolar liquid phase on gas chromatograph.

Length of the column 30 m, gas-carrier (helium) rate 40 cm/min. Measurements were carried out at temperatures 220°, 230°, 240° C. The data given in Table 2 demonstrate identity of retention times of the known and claimed crystalline modifications of the cited compound. The data presented make it possible to conclude that the crystalline modification of the invention has a chemical formula of the specified compound.

TABLE 2

Times of Gas Chromatographic Retention of the Known and Claimed Crystalline Modifications of 2-Dimethylaminoethyl-n-Butylamino-benzoate Hydrochloride

| Nos. | Compound | (220° C.) | (230° C.) | (240° C.) |
|---|---|---|---|---|
| 1 | Known crystalline modification | 15 12.0 | 11 21.1 | 8 42.9 |
| 2 | Crystalline modification of the invention | 15 11.6 | 11 21.3 | 8 43.0 |

To compare spectral characteristics of the known crystalline modification and the claimed modification of the specified Compound, their IR- and QR-spectra were measured.

IR-spectroscopic analysis was conducted in the frequency range of 400–4000 cm$^{-1}$ in KBr.

Characteristic IR-frequencies are given in Table 3.

TABLE 3

Characteristic IR-Frequencies of the Known Modification and the Claimed Crystalline Modification of 2-Dimethylaminoethyl-n-Butylaminobenzoate Hydrochloride IR-frequencies, cm$^{-1}$

| Known modification of the specified compound | Claimed modification of the specified compound |
|---|---|
| 3368 | 3368 |
| 3000–2800 | 3000–2800 |
| 1688 | 1688 |
| 1600,1580,1536 | 1600,1580,1534 |
| 1480 | 1480 |
| 1470–1400 | 1470–1400 |
| 1400–1300 | 1400–1300 |
| 1286,1276 | 1284 |
| 1174, 1167 | 1172 |
| 1144 | 1144 |
| 1126,1120, 1108 | 1124 |
| 1000–500 | 1000–500 |

As follows from Table 3, the main distinction of the IR-spectrum of the claimed crystalline modification from the known one consists in the absence of band splitting at 1284, 1172 and 1124 cm$^{-1}$.

QR-spectra were measured in the frequency range of of 10–2000 cm$^{-1}$. Characteristic QR-frequencies are given in Table 4.

TABLE 4

Characteristic QR-Frequencies of the Known and
Claimed Crystalline Modifications of
2-Dimethylaminoethyl-n-Butylaminobenzoate Hydrochloride
QR-frequencies, cm$^{-1}$

| Known modification of the specified compound | Claimed modification of the specified compound |
|---|---|
| 1691 | 1691 |
| 1597,1577,1534 | 1601 |
| 1376,1345,1309 | 1478 |
| 1273 | 1380,1351 |
| 1166 | 1280 |
| 1140 | 1177 |
| 920–630 | 1147 |
| 122,100,87,77 | 920–640 |
| 62,51,37,23 | 84,58,39 |

QR-spectra of modification of the invention significantly differ from QR-spectra of the known modification. It follows from Table 4 that the known modification has in the range of 150–10 cm$^{-1}$ a highly structured spectrum consisting of 8 bands with peaks at 122, 100, 87, 77, 62, 51, 37 and 23 cm$^{-1}$.

The claimed novel crystalline modification of the specified compound is characterized by only slightly manifested bands at 84, 58 and 39 cm$^{-1}$.

Thus, the data given above evidence that the compound of the invention is the novel crystalline modification of 2-dimethylaminoethyl-n-butylaminobenzoate hydrochloride. [Local anaesthetic activity of the claimed crystalline modification of the cited compound was studied in comparison with the known modification (preparation tetracaine widely used in microsurgery of eye).

To do this, 1% solution of the known preparation and 0.1, 0.2, 0.25 and 0.3% solutions of the claimed preparation in 0.9% solution of sodium chloride were prepared.

Investigations were carried out on 44 animals—chinchilla rabbits. Each of the listed solutions of the specified compound was administered dropwise in equal amount into a rabbit's eye and time of onset of anaesthesia and duration of anaesthesia were determined by a method of touching the cornea of the animal's eye. In all cases 0.06 ml of solution were administered dropwise into an eye (two 0.03 ml droplets). In 1.5 hour after recovery from anaesthesia, the rabbits were killed, the test eye was excerpted and subjected to electron microscopy and ordinary histological analysis. Duration of anaesthetic effect of 0.1%, 0.2%, 0.25% and 0.3% solutions of the claimed preparation was compared with duration of anaesthetic effect of the standard anaesthetic, that is 1% solution of the known preparation.

Experimental values of the time of onset of anaesthesia and dependence of duration of anaesthetic effect of all test solutions of the preparation on their concentration are presented in Table 5 ($\alpha=0.95$).

TABLE 5

| Nos. of tests 1 | Preparation 2 | Concentration of solution, % 3 | Number of animals 4 | Average time of anaethesia onset, s 5 | Average duration of anaesthesia, min 6 |
|---|---|---|---|---|---|
| 1 | Known preparation | 1 | 3 | 16.3 ± 3.2 | 48.0 ± 6.7 |
|   | Claimed preparation | 0.1 | 3 | 12.7 ± 1.5 | 13.4 ± 3.3 |
| 2 | Known preparation | 1.0 | 3 | 13.0 ± 1.0 | 43.1 ± 5.8 |
|   | Claimed preparation | 0.2 | 3 | 13.7 ± 2.0 | 33.0 ± 0.4 |
| 3 | Known preparation | 1.0 | 3 | 9.7 ± 1.5 | 51.8 ± 6.4 |
|   | Claimed preparation | 0.25 | 4 | 20.8 ± 0.7 | 32.1 ± 1.7 |
| 4 | Known preparation | 1.0 | 3 | 13.3 ± 6.0 | 61.3 ± 4.0 |
|   | Claimed preparation | 0.3 | 4 | 8.0 ± 1.5 | 55.2 ± 1.7 |

Influence of radial keratotomy on duration of anaesthetic effect of the test solutions of the specified compound was studied. The values of time of onset of anaesthesia caused by dicaine solutions in the coarse of keratotomy on rabbits are given in Table 6 ($\alpha=0.95$).

TABLE 6

| Nos. | Preparation | Concentration of solution, % | Average time of anaethesia onset, s | Average duration of anaesthesia, min |
|---|---|---|---|---|
| 1 | Dicaine | 1.0 | 11.3 ± 1.9 | 21.6 ± 0.4 |
| 2 | Claimed preparation | 0.3 | 11.3 ± 0.9 | 15.7 ± 0.5 |
| 3 | Claimed preparation | 0.25 | 11.0 ± 0.6 | 12.4 ± 0.3 |
| 4 | Claimed preparation | 0.1 | 15.0 ± 0.7 | 6.9 ± 0.5 |

When 0.1% solution of the compound of the invention was used, duration of complete anaesthesia allowed to carry out only three stages of a five-stage operation of keratotomy, i. e. marking, incisions of the cornea periphery and incisions to the central optical zone. After this, sensitivity of the eye to surgical instruments restored. When administering 0.25% and especially 0.3% solutions of the preparation of the invention, duration of anaesthesia was sufficient to perform all five stages of keratotomy lasting 3 minutes (i.e. controlling the depth and deepening of the insicion and lavage of the incision). When 0.25% and 0.3% solutions of the claimed compound were administered, the rabbit's eye was completely insensitive to surgical manipulations. 0.3% solution of the claimed preparation, as compared with 1% solution of the known preparation, provides, in the coarse of operation, similar intensity of anaesthesia sufficient to perform all stages of the operation.

It should be noted that a surgical operation reduces duration of anaesthesia in case of administering solutions of the claimed preparation of all concentrations under test, as well as of using 1% solution of the known preparation. However, reduction of duration of anaesthetic effect caused by the solution of the claimed preparation and solution of the known preparation proceeds to variable degrees: in case of administering 0.1% solution of the claimed preparation, duration of anaesthetic effect decreases on the average from 13 min to 7 min (46.2%); in case of 0.25% solution, from 32 min to 12 min (62.5%); in case of 0.3% solution, from 55 min to 16 min (70.9%), in , case of using 1% solution of the known preparation, from 51 min to 22 min (56.9%).

When 1% solution of the known preparation was administered into the rabbit's eye, the eye surface became undulated and dim. When the rabbit's eye was affected by the solution of the claimed preparation of all concentrations under test, no changes of the eye surface were observed, visually the test eye didn't differ from an intact one.

As a result of the tests conducted, a conclusion can be made that duration of anaesthetic effect of 0.3% solution of the claimed preparation and of 1% solution of the known preparation used in ophthalmosurgery is approximately equal and makes up, on the average, 55 min (difference 55.2±1.7 min and 61.3±4.0 min is not certain). With similar intensity of anaesthesia caused by 0.3% solution of the claimed compound and 1% solution of the known preparation, restoration of eye sensitivity, in case of administering solution of the preparation of the invention, proceeds faster than in case of using solution of the known preparation. 0.3% solution of the preparation of the invention equal in intensity and duration of anaesthetic effect to 1% solution of the known preparation, as distinct from the latter doesn't cause undulation and dimness of a surface of the rabbit's eye. After administering solutions of all the test concentrations, the eye visually doesn't differ from the intact one. 0.1%, 0.2% and 0.25% solutions of the preparation of the invention can be used for local anaesthesia of the eye in the coarse of various painful manipulations and procedures of short duration.

Thus, the data given evidence that the claimed crystalline modification of the specified compound shows increased local anaesthetic activity and reduced side effects. Indicated properties allow to decrease significantly a dosage of the preparation at enhanced therapeutical efficiency of the latter.

The claimed crystalline modification of the specified compound, according to the invention, is an active principle of the pharmaceutical preparation for anaesthesia of eyes.

The pharmaceutical preparation of the invention contains the active ingredient in amount of from 0.05 to 0.5% by mass and any pharmaceutical solvent appropriate for eye drops. Additionally, it may contain any derivative of alkylcellulose in amount of from 0.1 to 0.75% by mass, specifically water-soluble methylcellulose.

Selection of the concentration of the active ingredient is determined by the fact that within the indicated range of concentrations a high local anaesthetic effect is manifested without side actions.

The pharmaceutical preparation of the invention may contain any alkyl derivative of cellulose (methyl, ethyl, propyl, etc) as all of them cause an increase of droplets' viscosity which enhances the most efficient utilization of the active ingredient.

Selection of alkylcellulose concentration in the pharmaceutical preparation of the invention is determined by the fact that only within the indicated range such viscosity of pharmaceutical preparation is obtained which results in the best adhesion of the preparation to the tissue of the eyeball. At alkylcellulose concentration below 0.1%, viscosity of the claimed preparation is so low that drops administered into the eye freely flow out from under the eyelid.

At alkylcellulose concentration above 0.75%, viscosity increases to such extent that prevents uniform spreading of the claimed pharmaceutical preparation over the eyeball.

Preferable usage of methylcellulose is associated with the fact that it is most compatible with the active principle, efficiently releases the active principle from the pharmaceutical preparation and is widely used in medical practice.

For experimental studies of the claimed pharmaceutical preparation, various versions of the preparation were prepared.

Studies of local anaesthetic activity of the claimed pharmaceutical preparation compared to the known preparation were conducted on chinchilla rabbits. Each of the prepared solutions was administered dropwise in equal amounts into the rabbit's eye and time of onset of anaesthesia and its duration were determined using a method of touching the cornea of the animal's eye (Renier method). In all cases 0.06 ml of solution of the preparation were administered (two 0.03 ml droplets). In 1.5 hour after recovery from anaesthesia, the rabbits were killed, the eye was excerpted and subjected to histological analysis.

Data of experimental studies are presented in Table 7 ($\alpha=0.95$).

TABLE 7

| Nos. of tests 1 | Composition of pharmaceutical preparation, % by mass 2 | Average time of anaesthesia onset, seconds 3 | Average duration of anaesthesia, minutes 4 | Side effects 5 |
|---|---|---|---|---|
| 1 | Known preparation: active principle- 0.25, sodium chloride- 0.9, distilled water up to 100 | 13.4 ± 2.0 | 15.3 ± 2.0 | Surface of the eye becomes dim |
| 2 | Known preparation: | 13.0 ± 1.0 | 26.4 ± 3.2 | Surface of the |

TABLE 7-continued

| Nos. of tests 1 | Composition of pharmaceutical preparation, % by mass 2 | Average time of anaesthesia onset, seconds 3 | Average duration of anaesthesia, minutes 4 | Side effects 5 |
|---|---|---|---|---|
|  | active principle-0.5, sodium chloride-0.9, distilled water up to 100 |  |  | eye becomes undulated and dim |
| 3 | Known preparation: active principle-1.0, sodium chloride-0.9, distilled water up to 100 | 13.0 ± 1.0 | 48.0 ± 3.8 | Undulation and dimness increase |
| 4 | Preparation of the invention: active principle-0.05, sodium chloride-0.9, distilled water up to 100 | 15.0 ± 2.0 | 8.2 ± 1.5 | Not observed |
| 5 | Preparation of the invention: active principle-0.1, sodium chloride-0.9, distilled water up to 100 | 12.7 ± 1.5 | 13.4 ± 3.3 | Not observed |
| 6 | Preparation of the invention: active principle-0.3, sodium chloride-0.9, distilled water up to 100 | 8.0 ± 1.5 | 55.2 ± 1.7 | Not observed |
| 7 | Preparation of the invention: active principle-0.3, sodium chloride-0.9, methylcellulose-0.1, distilled water up to 100 | 5.3 ± 1.0 | 75.2 ± 3.0 | Not observed |
| 8 | Preparation of the invention: active principle-0.3, sodium chloride-0.9, methylcellulose-0.5, distilled water up to 100 | 5.0 ± 1.0 | 75.7 ± 3.5 | Not observed |
| 9 | Preparation of the invention: active principle-0.3, sodium chloride-0.9, methylcellulose-0.75, distilled water up to 100 | 4.0 ± 0.5 | 69.3 ± 2.1 | Not observed |

It follows from the table that the pharmaceutical preparation of the invention having high anaesthetic activity, practically doesn't cause side effects. High local anaesthetic activity of the active principle of the claimed pharmaceutical preparation allows to reduce concentration of the active principle in the preparation, as compared with the known preparation, by a factor of three and more and thus to decrease significantly toxicity of the preparation.

Preparation of the invention was tested in clinics on humans. The test was conducted during performing radial keratotomy. Three versions of pharmaceutical preparations were administered: 1% solution of the known preparation (on the base of the known modification of 2-di-methylamino-n-butylaminobenzoate hydrochloride) (Version 1); 0.25 and 0.3% solutions of the preparation of the invention (Versions 2 and 3) in the coarse of performing radial keratotomy. Solution of Version 1 was administered drop wise at each of the first three stages of the operation. In all patients without exception, cornea edema, desquamation of epithelium were observed, edema retained during 2 days after the operation.

Solution of Version 2 was employed for surface anaesthethesia of the eye in 28 patients. This solution was administered dropwise only once—at the first stage of the operation, but intensity of anaesthesia was deficient to perform the operation in part of the patients.

Solution of Version 3 was used for surface anaesthesia of the eye in 80 patients. This solution was administered also once at the first stage of the operation. Anaesthesia was efficient to carry out the operation. Residual phenomena of tactile sensitivity without painful sensations, not preventing to perform the operation were observed in 5 patients, (6.2%). On the average, to perform an operation on a patient, 5 ml of 1% solution of the known preparation and only 0.1 ml of 0.25% and 0.3% solutions of the preparation of the invention were used.

As a result of the tests conducted it was found that the anaesthetic effect of 0.3% solution of the claimed preparation, the preparation volume being reduced 50-fold in the coarse of performing keratotomy, corresponds to the anaesthetic effect of 1% solution of the known preparation. Administration of said solution of the claimed preparation doesn't cause edema of the eyelid in all the patients, as distinct from the employment of the known preparation.

The pharmaceutical preparation for anaesthesia of eyes, according to the invention, is a transparent, colourless liquid, pH 4.3–6.8.

The claimed preparation is produced according to the known techniques.

The preparation of the invention is stored at a temperature of 25° C. at a light-proof place. Storage life is 12 months.

After 6 and 12 months of storage, the preparation of the invention was analysed for validity.

Results of the analysis demonstrate that after 12 months of storage, the main properties of the claimed preparation haven't changed which allows to make a conclusion on the validity of the preparation.

The claimed pharmaceutical preparation for anaesthesia of eyes allows to reduce the number of post-operative complications due to the absence of side effects, to decrease toxicity on account of reduced concentration of the active ingredient in the preparation with retention of local anaesthetic effect and prolonged term of validity up to 12 months (term of validity of the known preparation is 3 months).

According to the invention, the active ingredient of the claimed preparation—a novel crystalline modification of 2-dimethylaminoethyl-n-butylaminobenzoate hydrochloride is produced by way of cooling solution of the indicated compound of a polymorphic form in water or in an organic solvent, or their mixture by a cooling agent at a rate of no less than 8° C./min till its complete crystallization, with subsequent isolation of obtained crystals and their drying.

As a cooling agent use is made of any substance capable to reduce a temperature of the compound being cooled at a rate of no less than 8° C./min. The best suitable substance used as a cooling agent is liquid nitrogen, its utilization allows to increase yield of the base product due to fast gain and further maintenance of the necessary rate of cooling.

Selection of the cooling rate of the initial solution of said compound is determined by the fact that the object set forth (production of a novel crystalline modification) is attained at a cooling rate of no less than 8° C./min. Conducting a process of crystallization at a cooling rate below 8° C./min fails to produce the claimed novel crystalline modification.

The upper level of the cooling rate is not limited. At any maximum attainable cooling rate of the initial solution, formation of the novel crystalline modification proceeds.

Process of cooling is carried out in water or any organic solvent, or in their mixture in which the initial compound is soluble. The best suited solvents in which the initial compound is well soluble are water and ethanol. In doing so, the best yield of the base product is attained.

The claimed modification can be produced irrespective of the concentration of the initial compound in the solution.

Selection of the drying conditions at a pressure of no more than $10^{-2}$ mm Hg is determined by the fact that the ready dried product should have humidity no more than 3%.

Drying at a pressure higher than $10^{-2}$ mm Hg gives a damp spreading unstable mass.

For better understanding of the present invention, given below are the following examples of producing the claimed modification.

EXAMPLE 1

500 ml of 10% aqueous solution of 2-dimethylaminoethyl-n-butylaminobenzoate hydrochloride (polymorphic form) were cooled by liquid nitrogen at a cooling rate of 8° C./rain till complete crystallization. The obtained frozen mass was put on pans and charged in a sublimator. Drying was carried out at $10^{-2}$ mm Hg to residual humidity of 3%. Yield of the base product–9.75% by mass The obtained compound was characterized by the values of interplanar spacings d and relative intensities of reflections I coinciding with the corresponding indicated values of the novel crystalline modification of 2-dimethylaminoethyl-n-butylaminobenzoate hydrochloride having melting point 148.6°±0.3° C. with a single endothermal effect. In all indices (NMR, IR-, QR-spectra), the obtained compound corresponded to the claimed novel crystalline modification.

EXAMPLE 2

The process was conducted in a manner similar to that of Example 1, concentration of the initial compound in water was 5% by mass.

Yield of the base product 96.2% by mass.

The obtained compound having melting point 148.6°±0.3° C. with a single endothermal effect had characteristics similar to those of Example 1.

EXAMPLE 3

The process was conducted in a manner similar to that of Example 1, cooling rate being equal to 300° C./min.

Yield of the base product 97.5% by mass.

The obtained compound having melting point 148.6°±0.3° C. with a single endothermal effect had characteristics similar to those of Example 1.

EXAMPLE 4

The process was conducted in a manner similar to that of Example 1, drying was carried out in a sublimator at a pressure of $10^{-5}$ mm Hg.

Yield of the base product 96.8% by mass.

The obtained compound had characteristics similar to those of Example 1.

EXAMPLE 5

500ml of 10% solution of 2-dimethylaminoethyl-n-butylaminobenzoate hydrochloride (polymorphic form) was cooled by liquid nitrogen at a rate of 8° C./min till complete crystallization of the solution. Produced frozen mass was put on pans and charged in a sublimator. Drying was carried out at $10^{-2}$ mm Hg.

Yield of the base product 95.6% by mass.

In all indices, the obtained compound corresponded to the compound of Example 1 with melting point 148.6°±0.3° C. and a single endothermal effect.

EXAMPLE 6

The process was conducted in a manner similar to that of Example 5, concentration of initial compound in ethanol being 50% by mass.

Yield of the base product 97.0% by mass.

The obtained compound had characteristics similar to those of Example 1.

EXAMPLE 7

The process was carried out in a manner similar to that of Example 5, at a cooling rate of 300° C./min. Yield of the base product 98.2% by mass.

The obtained compound had characteristics similar to those of Example 1.

EXAMPLE 8

The process was carried out in a manner similar to that of Example 5, drying being conducted in a sublimator at a pressure $10^{-5}$ mm Hg. Yield of the base product 96.3% by mass.

The obtained compound had characteristics similar to those of Example 1.

EXAMPLE 9

500 ml of 1% solution of the initial compound in water-ethanol mixture (1:1) were taken. The process was carried out in a manner similar to that of Example 5. Yield of the base product 96.0% by mass.

The obtained compound had characteristics similar to those of Example 1.

INDUSTRIAL APPLICABILITY

Crystalline modification of 2-dimethylaminoethyl-n-butylaminobenzoate hydrochloride according to the invention possesses a local anaesthetic effect and can be widely used in various fields of medicine, particularly pharmaceutical preparation for anaesthesia of eyes based on the claimed compound can find application in ophthalmology in the coarse of performing surgical operations.

I claim:

1. A method of making a crystalline modified 2-dimethylaminoethyl-n-butylamino benzoate hydrochloride having a single, endothermal effect of melting at 148.6°±0.3° C. and the following values of interplanar spacing d and relative intensities of reflections I:

| I | d,Å | I | d,Å |
|---|---|---|---|
| 3 | 26.140 | 4 | 2.824 |
| 100 | 12.755 | 2 | 2.798 |
| 27 | 8.538 | 1 | 2.762 |
| 6 | 6.380 | 2 | 2.744 |
| 2 | 6.117 | 2 | 2.678 |
| 6 | 5.644 | 1 | 2.631 |
| 12 | 5.491 | 1 | 2.570 |

-continued

| I | d,Å | I | d,Å |
|---|---|---|---|
| 56 | 5.096 | 1 | 2.534 |
| 17 | 4.874 | 1 | 2.514 |
| 10 | 4.486 | 1 | 2.454 |
| 15 | 4.244 | 1 | 2.419 |
| 7 | 4.418 | 1 | 2.346 |
| 1 | 4.137 | 1 | 2.308 |
| 5 | 4.001 | 1 | 2.256 |
| 3 | 3.949 | 1 | 2.232 |
| 5 | 3.828 | 1 | 2.166 |
| 3 | 3.585 | 1 | 2.008 |
| 7 | 3.515 | 2 | 1.953 |
| 3 | 3.427 | 1 | 1.691 |
| 3 | 3.341 | 1 | 1.584 |
| 3 | 3.310 | | |
| 3 | 3.170 | | |
| 4 | 3.156 | | |
| 4 | 3.149 | | |
| 1 | 3.064 | | |
| 2 | 2.979 | | |
| 1 | 2.944 | | |
| 1 | 2.903 | | | said method comprising:

a) cooling a solution of 2-dimethylaminoethyl-n-butylaminobenzoate hydrochloride of polymorphic form using a cooling agent at a rate of no less than 8° C./minute until the solution has substantially completely crystallized to form crystals and b) isolating the crystals so formed, wherein the solution cooled in step a comprises a solvent selected from the group consisting of water, and organic solvent and a mixture thereof.

2. A method according to claim 1 wherein ethanol is used as an organic solvent.

3. A method according to claim 1, wherein the cooling agent is capable itself of effecting said minimum cooling rate and the drying is carried out in vacuo at a pressure of no more than $10^{-2}$ mm Hg.

4. A method according to claim 3, wherein the cooling agent is liquid nitrogen.

5. A method as claimed in claim 1, wherein the method further comprises drying the isolated crystals.

6. A method as claimed in claim 5, wherein the solution cooled in step a comprises ethanol.

7. A method as claimed in claim 6, wherein the cooling agent is capable itself of effecting said minimum cooling rate.

8. A method as claimed in claim 7, wherein the drying is carried out in vacuo at a pressure of no more than $10^{-2}$ mm Hg.

9. A method according to claim 7, wherein the cooling agent is liquid nitrogen.

10. A method according to claim 1, wherein the cooling agent is liquid nitrogen.

* * * * *